United States Patent [19]
Craig

[11] 4,108,168
[45] Aug. 22, 1978

[54] HIP SPLINT DEVICE

[76] Inventor: William A. Craig, 326 Viewcrest Rd., Glendale, Calif. 91202

[21] Appl. No.: 767,350

[22] Filed: Feb. 10, 1977

[51] Int. Cl.² .............................................. A61F 3/00
[52] U.S. Cl. ................. 128/80 A; 128/87 C; 128/134
[58] Field of Search ............... 128/87 R, 87 C, 80 R, 128/80 A, 134, DIG. 15

[56] References Cited

U.S. PATENT DOCUMENTS

| | | | |
|---|---|---|---|
| 3,114,368 | 12/1963 | Richmond | 128/87 C |
| 3,315,671 | 4/1967 | Creelman | 128/134 |
| 3,358,141 | 12/1967 | Hoffmann et al. | 128/DIG. 15 X |
| 3,423,773 | 1/1969 | Yamate | 128/80 R X |
| 3,563,601 | 2/1971 | Dickey | 128/80 A X |
| 3,730,177 | 5/1973 | Thum | 128/80 A |

FOREIGN PATENT DOCUMENTS

| | | | |
|---|---|---|---|
| 1,240,222 | 5/1967 | Fed. Rep. of Germany | 128/87 C |
| 298,193 | 11/1965 | Netherlands | 128/87 C |
| 229,743 | 2/1969 | U.S.S.R. | 128/87 C |

Primary Examiner—John D. Yasko
Attorney, Agent, or Firm—John Joseph Hall

[57] ABSTRACT

A congenital hip splint device with easily adjustable shoulder harness means for securing a child's shoulders and torso so a back support and with easily adjustable thigh cuff members pivotally attached to thigh cuff anchoring members for securing a child's thighs in a hip flexion position from above 90° to lower angles as desired over a period of time.

9 Claims, 6 Drawing Figures

U.S. Patent     Aug. 22, 1978     Sheet 1 of 2     4,108,168
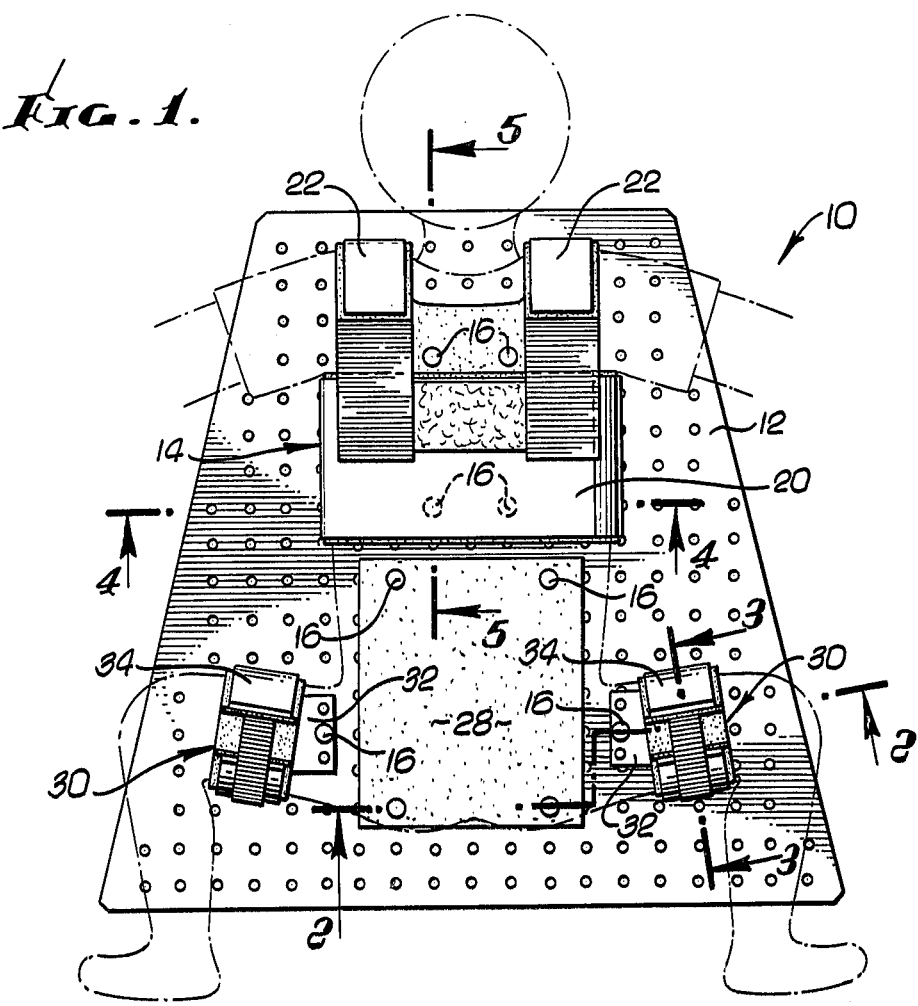
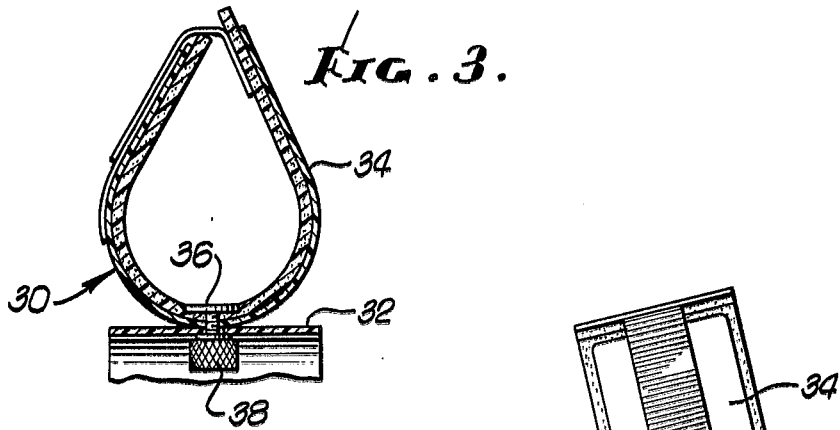
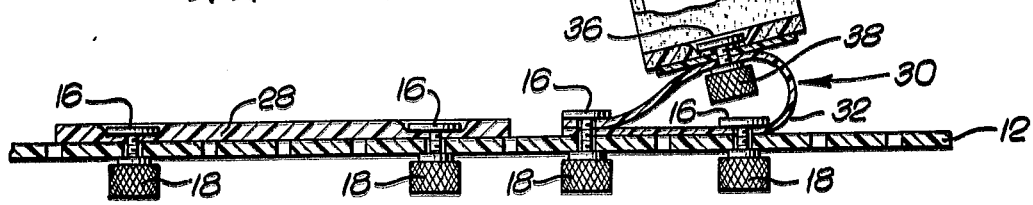

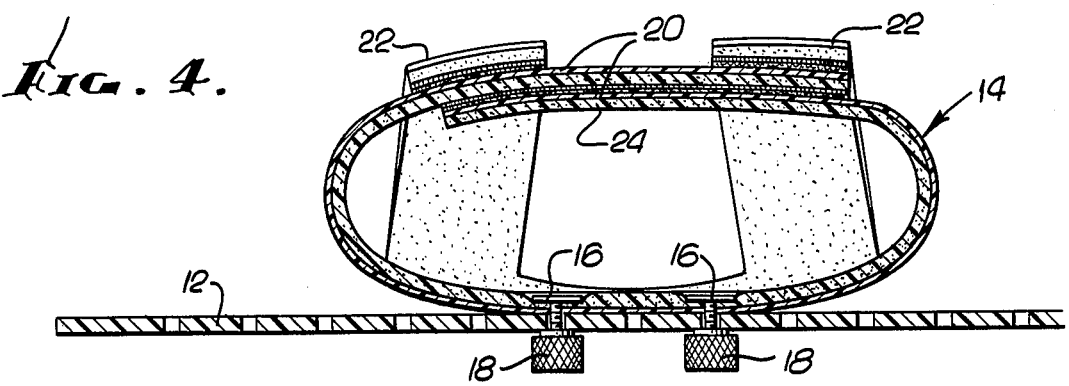
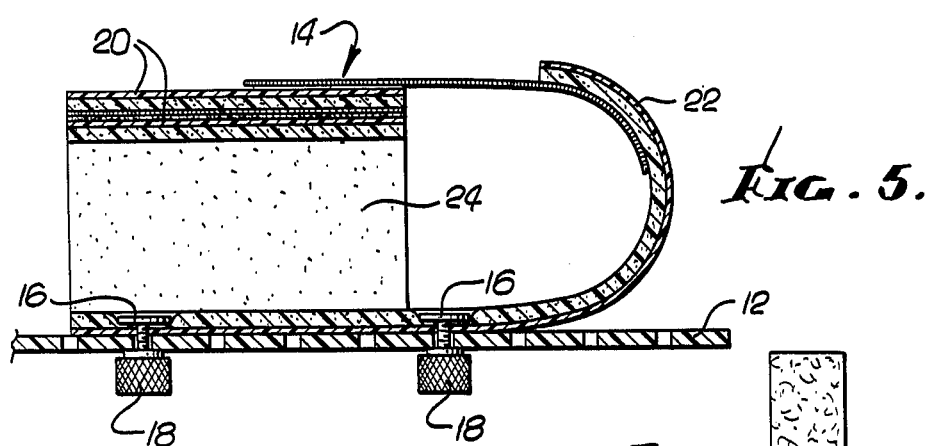
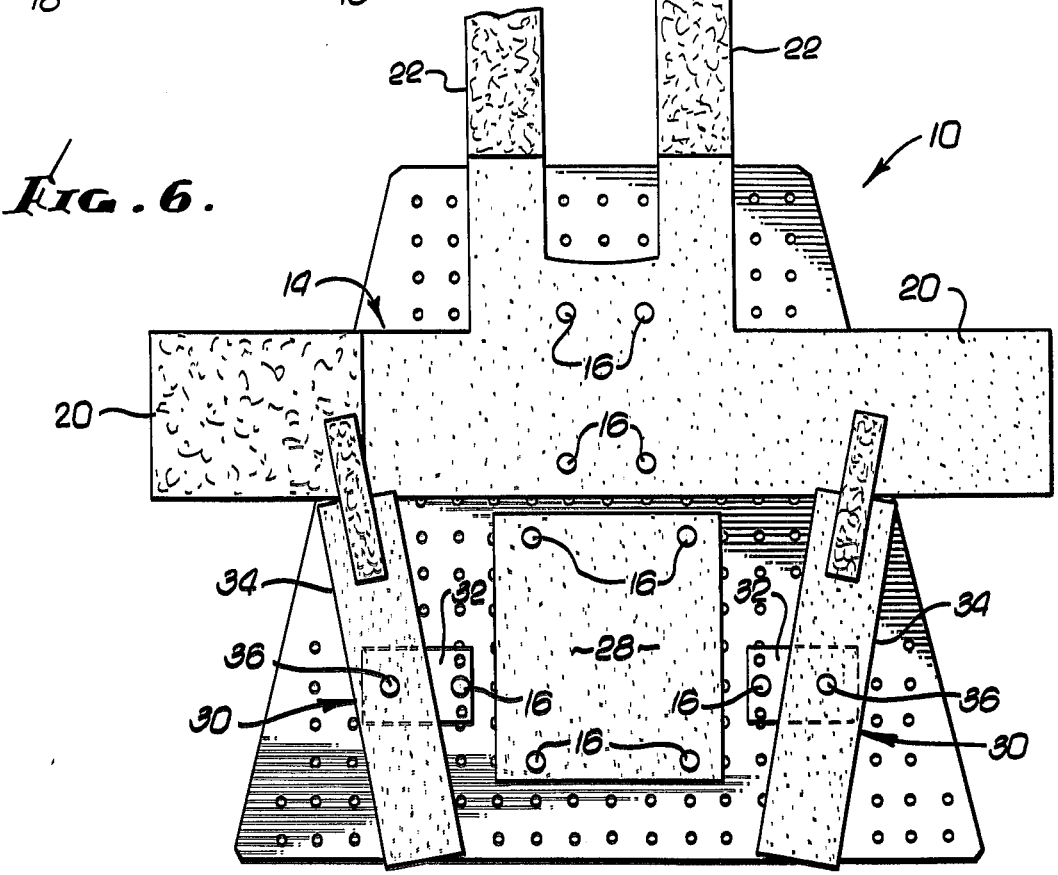

HIP SPLINT DEVICE

SUMMARY OF THE INVENTION

This invention relates to a device for use in the treatment of infants and small children ranging in age from about 6 months to about 2½ years who have a congenital hip condition which can be corrected by maintaining the hip in a flexed position for a period of time. The invention comprises a pegboard type of back support to which a shoulder harness is removably mounted. The shoulder harness has chest flap members and shoulder strap members fastened together by a velcro fastener for holding a child's shoulder in position and which can be adjusted easily for various chest diameters.

The thighs of the child are maintained in a flexed position by thigh cuff members pivotally attached to thigh cuff anchoring members which are removably fastened to the back support.

By adjusting the location of the thigh cuff anchoring members, and by adjusting the pivot angle of the thigh cuff members, a child's thighs may be flexed above 90° into a position known as a full frog position, which is required for successful treatment of a congenital hip condition. As treatment progresses, the hip flexion can be reduced as desired by easy and ready adjustment of the location of the thigh cuff anchoring members and of the angle of the thigh cuff members. Adjustments of the shoulder harness and thigh cuff members and thigh cuff anchoring members can be made to adapt to the growth of the child if needed.

My invention has a flexibility and ease of adjustment which is lacking in a cast and in other prior art devices. My invention can be easily used in various phases of treatment for a congenital hip condition from the full frog position, that is, a hip flexion of above 90°, to an extended abducted internally rotated position. My invention also avoids the discomfort and rigidity of a cast and of other prior art devices.

An object of this invention is to provide a hip splint device which easily maintains a small child in a hip flexion position over 90° without the discomfort of a cast or other prior art devices used in the treatment of a congenital hip condition.

Another object of this invention is to provide a hip splint device which can be easily adjusted for treatment of a congenital hip condition in a small child from a hip flexion of over 90° to an extended abducted internally rotated position.

A further object of this invention is to provide a hip splint device which can be easily adjusted to accomodate children from the age of about 6 months to about 2½ years without the discomfort of a cast or other prior art devices used in the treatment of a congenital hip condition.

A still further object of this invention is to provide a hip splint device which maintains a small child in a hip flexion position of over 90° to correct a congenital hip condition such as a hip dislocation without completely stretching the adductor muscles in the inside of the thigh.

These and other objects will be more readily understood by reference to the following description and claims, taken in conjunction with the accompanying drawings, in which FIG. 1 is a front elevational view of an embodiment of the invention with a child in position thereon.

FIG. 2 is a view taken along line 2—2 of FIG. 1.

FIG. 3 is a view taken along line 3—3 of FIG. 1.
FIG. 4 is a view taken along line 4—4 of FIG. 1.
FIG. 5 is a view taken along line 5—5 of FIG. 1.
FIG. 6 is a front elevational view of an embodiment of the invention with its elements in a flat or planar position.

The hip splint device has a pegboard back support member 12 preferably made of a suitable plastic such as polyethylene. A shoulder harness 14 is removably mounted with screws 16 and nuts 18, preferably made of nylon or other suitable plastic, at the top portion of the support member 12. The shoulder harness 14 has a pair of flexible chest flap members 20 and a pair of flexible shoulder strap members 22, preferably made of a suitable plastic like polyethylene and provided with an inner lining of nylon-covered corset padding 24 or other suitable material.

The strap members 22 and chest flap members 20 are provided with velcro fasteners for securing the strap members 22 to the chest flap members 20. However, any suitable type of fastening means may be used to secure the strap members 22 to the chest flap members 20. The shoulder harness 14 may be made from any suitable flexible material.

The lower portion of the support member 12 is provided with a pad member 28, preferably made of nylon-covered corset padding or other suitable material, removably mounted thereon with screws 16 and nuts 18.

A thigh cuff anchoring member 30 in the form of a loop 32 is removably mounted with screw 16 and nut 18 to the support member 12 on each lateral side of the pad member 28.

The height of the thigh cuff anchoring member 30 may be varied as needed in the course of treatment of the patient. The thigh cuff anchoring members 30 are preferably made of polyethylene plastic, although any suitable material may be used as well.

A thigh cuff member 34 is pivotally mounted by a screw 36 and nut 38 to each thigh cuff anchoring member 30, and is provided with velcro fastening means 40 at its ends. The thigh cuff members 34 are preferably made of flexible polyethylene plastic with an inner lining of nylon-covered corset padding, although various other suitable materials may be used as well.

In operation to correct congenital hip conditions such as a hip dislocation, the hip splint device 10 is prepared to receive a small child as shown in FIG. 1. The shoulder harness 14 is located and mounted on the back support member 12 in a position so that shoulder harness 14 secures the child's shoulders and torso to the back support member 12 when the shoulder strap members 22 are fastened to the chest flap members 20. The thigh cuff anchoring members 30 are located and mounted on the back support member 12 and on each side of pad member 28 so that the child's thighs are secured in a frog position when the thigh cuff members 34 are fastened together. The location of the thigh cuff anchoring members 30 may be adjusted as desired to maintain a hip flexion of the child above 90°, thereby maintaining the hips in a frog abduction position although a completely flat position of the hips is avoided by the height of the loops 32 of the thigh cuff anchoring members 30.

In this manner, the femoral head is maintained in position inside the acetabulum, the cup-shaped socket of the hip bone that receives the femoral head, thereby reducing a hip dislocation without completely stretching out the adductor muscles on the inside of the thigh. Reducing treatment generally begins with a height of the loops 32 being about 2 inches and then being reduced to about one inch high as treatment progresses.

The flexible shoulder harness 14 is easily adjustable both as to location and as to chest diameter of the child, and avoids the rigidity of a cast, thereby increasing the child's comfort. Similarly, the flexible thigh cuff members 34 may be easily adjusted both as to location and as to thigh diameter of the child, thereby avoiding the rigidity of a cast, increasing the child's comfort, and avoiding any possible interference with blood supply.

The invention may be modified to add an extension of the pegboard back support member 12 which would accomodate a larger child and also an ankle cuff member similarly constructed to the thigh cuff member 34 for internal rotation of the child's legs.

Although I have described a preferred embodiment of my invention, it is understood that numerous modifications in construction and arrangement of parts may be made within the scope of the invention as hereinafter claimed.

I claim:

1. A hip splint device for maintaining hip flexion above 90° in the treatment of congenital hip conditions in small children comprising:
    a planar support member;
    adjustable shoulder harness means removably mounted on the upper portion of said back support member;
    a pair of spaced thigh cuff anchoring members mounted on said back support member below said shoulder harness means, each of said thigh cuff anchoring members including a loop member; and
    a pair of thigh cuff members each pivotally mounted to each of said loop members of said thigh cuff anchoring members and having fastening means, said thigh cuff members being adapted to maintain hip flexion of a child's hips above 90°.

2. A hip splint device according to claim 1 in which each of said loop members is adjustable and raises each of said thigh cuff members to a distance ranging from about one to about two inches above the surface of the back support member.

3. A hip splint device according to claim 1 in which the shoulder harness means includes a pair of chest strap members and a pair of shoulder strap members and fastening means for fastening said chest strap members and said shoulder strap members together.

4. A hip splint device according to claim 3 in which the fastening means of the shoulder harness means is adjustable to accomodate varying chest diameters.

5. A hip splint device for maintaining hip flexion above 90° in the treatment of congenital hip conditions in small children comprising:
    a planar back support member having perforations therein;
    adjustable shoulder harness means removably mounted on the upper portion of said back support member;
    a pair of spaced thigh cuff anchoring members removably mounted on said back support member below said shoulder harness means, each of said thigh cuff anchoring members including a loop member, and
    a pair of thigh cuff members each removably and pivotally mounted to each of said loop members of said thigh cuff anchoring members and having means, said thigh cuff members being adapted to maintain hip flexion above 90°.

6. A hip splint device according to claim 5 in which each of said loop members is adjustable and raises each of said thigh cuff members to a distance ranging from about one to about two inches above the surface of the back support member.

7. A hip splint device according to claim 5 in which the shoulder harness means includes a pair of chest strap members and a pair of shoulder strap members and fastening means for fastening said chest strap members and said shoulder strap members together.

8. A hip splint device according to claim 5 in which the fastening means of the shoulder harness means is adjustable to accomodate varying chest diameters.

9. In a hip splint device for correction of a congenital hip condition in a small child, of the type having a shoulder harness means and thigh securing means, the improvement comprising:
    a planar back support member, on which said shoulder harness means is removably mounted;
    a pair of spaced thigh cuff anchoring members mounted on said planar back support member below said shoulder harness means, each of said thigh cuff anchoring members including an adjustable loop member to which said thigh securing means is pivotally mounted; whereby,
    hip flexion of said child's hips is maintained above 90° in the absence of a completely flat position of said hips against said planar back support member.

* * * * *